United States Patent [19]

Hidaka et al.

[11] Patent Number: 5,059,692

[45] Date of Patent: Oct. 22, 1991

[54] NOVEL COMPOUNDS EXHIBITING A VASODILATING ACTIVITY AND INHIBITORY ACTIVITY FOR PLATELET AGGREGATION

[76] Inventors: Hiroyoshi Hidaka, 1105-1-5-104, Hachimanyama, Tenpaku-ku, Nagoya-shi, Aichi-ken; Tomohiko Ishikawa, 2-C, Kohpo-Ogawa, 1-64-12, Fukiago-cho, Showa-ku, Nagoya-shi, Aichi-ken; Tsutomu Inoue, 1-8-2-201, Futawanishi, Funabashi-shi, Chiba-ken; Masayuki Yuasa, 3-25-5-103, Showa-machi, Akishima-shi, Tokyo-to; Takashi Inaba, 3-5-11-403, Sakae-cho, Higashimurayama-shi, Tokyo-to; Kenji Naito, 5-7-6-106, Matsubara-cho, Akishima-shi, Tokyo; Osamu Sakuma, 2-40-3-1105, Sekido, Tama-shi, Tokyo-to; Tadashi Morita, 2-9-10, Minamigashiwa, Kashiwa-shi, Chiba-ken; Shinpei Kidokoro, 6-27-16, Daita, Setagaya-ku, Tokyo-to, all of Japan

[21] Appl. No.: 574,730

[22] Filed: Aug. 30, 1990

[30] Foreign Application Priority Data

Sep. 1, 1989 [JP] Japan ................................. 1-224374
Sep. 12, 1989 [JP] Japan ................................. 1-234793

[51] Int. Cl.$^5$ .................. C07D 455/04; C07D 513/16
[52] U.S. Cl. ...................................... 546/80; 546/89; 546/90
[58] Field of Search .......................... 546/80, 89, 90; 514/293

[56] References Cited

U.S. PATENT DOCUMENTS 4,064,247 12/1977 Farge et al. ........................... 546/89

OTHER PUBLICATIONS

Yang et al., "The First Synthesis of . . . ", J. Heter. Chem. 26(3), 865-8 (1989).

Primary Examiner—C. Warren Ivy
Assistant Examiner—Celia chang
Attorney, Agent, or Firm—Sughrue, Mion, Zinn, Macpeak & Seas

[57] ABSTRACT

Novel compounds represented by the formula:

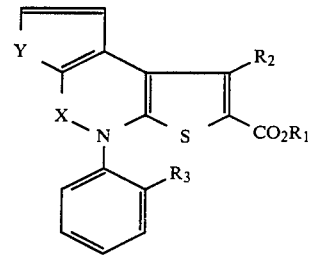

wherein $R_1$ represents an alkyl group having 1 to 3 carbon atoms, $R_2$ represents an amino group or a group of formula

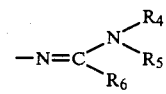

in which $R_4$ represents an alkyl group having 1 to 3 carbon atoms, $R_5$ represents an alkyl group having 1 to 3 carbon atoms or may combine with $R_6$ to form a five or six membered ring containing 4 to 5 carbon atoms, $R_6$ represents a hydrogen atom or may combine with $R_5$ to form a five or six membered ring containing 4 to 5 carbon atoms, $R_3$ represents a hydrogen atom, an alkyl group having 1 to 3 carbon atoms or a halogen atom, X represents a carbonyl group or a methylene group, Y represents a sulfur atom or a vinylene group and pharmaceutically acceptable salts thereof which exhibit a vasodilating activity and inhibitory activity for platelet aggregation. Thus, they are useful as therapeutic agents for treatment of angina pectoris, hypertension, throbosis and the like.

11 Claims, No Drawings

NOVEL COMPOUNDS EXHIBITING A VASODILATING ACTIVITY AND INHIBITORY ACTIVITY FOR PLATELET AGGREGATION

FIELD OF THE INVENTION

The present invention relates to novel compounds being useful as therapeutic agents. More particularly, the present invention relates to compounds represented by the formula (I):

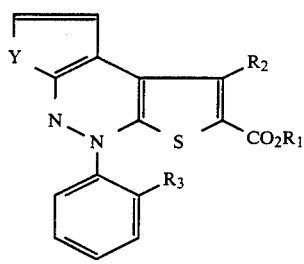

wherein $R_1$ represents an alkyl group having 1 to 3 carbon atoms, $R_2$ represents an amino group or a group of formula

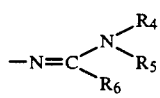

in which $R_4$ represents an alkyl group having 1 to 3 carbon atoms, $R_5$ represents an alkyl group having 1 to 3 carbon atoms or may combine with $R_6$ to form a five or six membered ring containing 4 to 5 carbon atoms, $R_6$ represents a hydrogen atom or may combine with $R_5$ to form a five or six membered ring containing 4 to 5 carbon atoms, $R_3$ represents a hydrogen atom, an alkyl group having 1 to 3 carbon atoms or a halogen atom, X represents a carbonyl group or a methylene group, Y represents a sulfur atom or a vinylene group and pharmaceutically acceptable salts thereof which exhibit a vasodilating activity and inhibitory activity for platelet aggregation. Thus, they are useful as therapeutic agents for treatment of angina pectoris, hypertension, thrombosis and the like.

BACKGROUND OF THE INVENTION

Anticoagulants such as heparin exhibiting antithrombin activity, fibrinolytic agents comprising urokinase and/or tissue plasminogen activators of every kind, and antiplatelet agents have been employed for treatment of thrombosis.

Of these drugs, antiplatelet agents are made up of agents of various sorts; That is, agents preventing a reduction of a platelet cyclic AMP level, which increase a concentration of the cyclic AMP or inhibit a decomposition of the cyclic AMP, agents inhibiting a production of thromboxane $A_2$ ($TXA_2$) which causes platelet aggregation, agents inhibiting $TXA_2$ activity, agents raising a level of prostaglandin $I_2$ ($PGI_2$) which inhibits platelet aggregation, and agents bringing on a prolongation of $PGI_2$ activity, are involved as antiplatelet agents, and these agents had been developed and have been used as therapeutic agents.

However, of the agents stated above, agents which raise a $PGI_2$ level or which bring on a prolongation of $PGI_2$ activity, are very unstable, and only their analogues are being developed in form of an inclusion compound.

On the other hand, inhibitors on $TXA_2$ activities, which are a $TXA_2$ receptor antagonist, inhibit a production of platelet $TXA_2$ which is produced from a phospholipid via arachidonic acid, prostaglandin $G_2$ and prostaglandin $H_2$, enhancing and stimulating a production of $PGI_2$ in blood vessel walls, however, they have a weak point on their stabilities.

SUMMARY OF THE INVENTION

An object of the present invention is to provide novel compounds and pharmaceutically acceptable salts thereof which exhibit a vasodilating activity and inhibitory activity for platelet aggregation.

Another object of the present invention is to provide a method for treatment of angina pectoris, hypertension, thrombosis and the like by using them.

Other objects, features and advantages of the present invention will be apparent from the following description of the invention.

DETAILED DESCRIPTION OF THE INVENTION

The present invention provides novel compounds and pharmaceutically acceptable salts thereof which exhibit a vasodilating activity and inhibitory activity for platelet aggregation. Thus, they are useful as therapeutic agents for treatment of angina pectoris, hypertension, thrombosis and the like.

The compounds of the present invention are novel compounds, and can easily be prepared by the following manner: That is, of the compounds represented by the formula (I), compounds wherein X represents a carbonyl group and $R_2$ represents an amino group, represented by the formula (Ia):

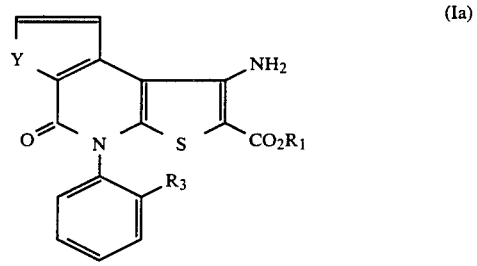

wherein $R_1$ represents an alkyl group having 1 to 3 carbon atoms, $R_3$ represents a hydrogen atom, an alkyl group having 1 to 3 carbon atoms or a halogen atom and Y represents a sulfur atom or a vinylene group; can be prepared by reacting an ester compound represented by the formula (II):

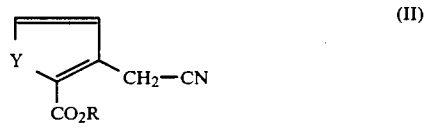

wherein R represents an alkyl group having 1 to 6 carbon atoms and Y has the same meaning as defined above; with an isothiocyanate compound represented by the formula (III):

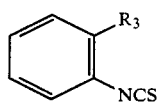

wherein $R_3$ represents an alkyl group having 1 to 3 carbon atoms or a halogen atom to obtain a compound represented by the formula (IV):

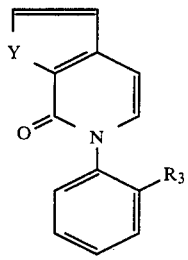

wherein $R_3$ and Y have the same meanings as defined above, and then treating the obtained compound with alkyl bromoacetate having 3 to 5 carbon atoms in the presence of a basic substance such as sodium hydride and potassium t-butoxide.

The compounds represented by the formula (Ib):

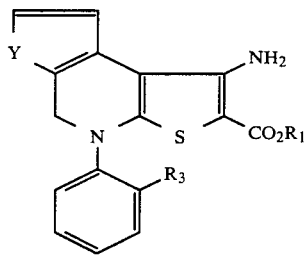

wherein $R_1$ represents an alkyl group having 1 to 3 carbon atoms, $R_3$ represents a hydrogen atom, an alkyl group having 1 to 3 carbon atoms or a halogen atom and Y represents a sulfur atom or a vinylene group; can be prepared by reducing a compound represented by the formula (Ia) in an inert organic solvent such as tetrahydrofuran and ether, in the presence of a reductant such as lithium aluminium hydride, aluminium chloride, lithium chloride and sodium borohydride.

The compounds represented by the formula (Ic):

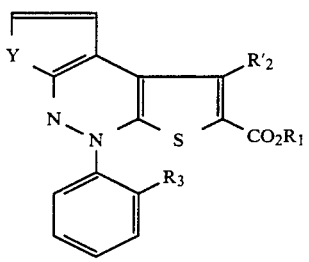

wherein $R_1$ represents an alkyl group having 1 to 3 carbon atoms, $R'_2$ represents a group of formula

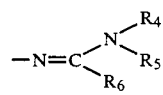

in which $R_4$ represents an alkyl group having 1 to 3 carbon atoms, $R_5$ represents an alkyl group having 1 to 3 carbon atoms or may combine with $R_6$ to form a five or six membered ring containing 4 to 5 carbon atoms, $R_6$ represents a hydrogen atom or may combine with $R_5$ to form a five or six membered ring containing 4 to 5 carbon atoms, $R_3$ represents a hydrogen atom, an alkyl group having 1 to 3 carbon atoms or a halogen atom, X represents a carbonyl group or a methylene group and Y represents a sulfur atom or a vinylene group; can be prepared by treating a compound represented by the formula (Ia) or (Ib) with an amide compound such as dimethyl formamide, diethylformamide and N-methyl-2-pyrrolidone in the presence of phosphorus oxychloride or thionyl chloride.

Of the ester compounds represented by the formula (II) used in the present invention as starting materials, the compound wherein Y represents a sulfur atom, represented by the formula (IIa):

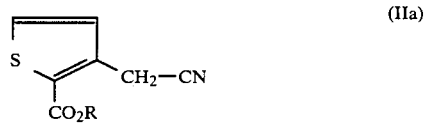

wherein R represents an alkyl group having 1 to 6 carbon atoms; can be easily prepared by a similar method described in literature.

The ester compounds represented by the formula (II) other than compounds represented by the formula (IIa) are commercially available or can be prepared by a similar method to that described in literature.

The compounds represented by the formula (II) used in the present invention are also commercially available or can be prepared by a similar method to that described in literature.

The compounds represented by the formula (I) of the present invention can be converted into pharmaceutically acceptable salts thereof according to a usual manner.

Examples of such salts include a hydrochloric acid salt, a sulfonic acid salt, a p-toluenesulfonic acid salt, an acetic acid salt, a citric acid salt, a succinic acid salt, a tartaric acid salt, a fumaric acid salt and the like.

Of the compounds represented by the formula (I) of the present invention, methyl 1-amino-4,5-dihydro-5-oxo-4-phenyl-thieno[2,3-c]isoquinoline-2-carboxylate, methyl 1-amino-4,5-dihydro-4-(2-methylphenyl)-5-oxo-thieno[2,3-c]isoquinoline-2-carboxylate, methyl 1-amino-4,5-dihydro-4-phenyl-thieno[2,3-c]isoquinoline-2-carboxylate, methyl 1-amino-4,5-dihydro-5-oxo-4-phenyl-dithieno[2,3-b:3',2'-d]pyridine-2-carboxylate and methyl 1-amino-4-(2-chlorophenyl)-4,5-dihydro-5-oxo-thieno[2,3-c]isoquinoline-2-carboxylate are preferable, and the most preferable compounds are methyl 1-amino-4,5-dihydro-4-(2-methylphenyl)-5-oxo-thieno[2,3-c]isoquinoline-2-carboxylate, methyl 1-amino-4,5-dihydro-5-oxo-4-phenyl-thieno[2,3-c]isoquinoline-2-carboxylate and methyl 1-amino-4,5-dihydro-4-phenyl-thieno[2,3-c]isoquinoline-2-carboxylate.

The compounds represented by the formula (I) of the present invention and pharmaceutically acceptable salts thereof can be administered in various dosage forms depending upon the intended therapy. Typical dosage forms which can be used are tablets, pills, powders, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrators such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, the resulting solution and suspension are preferably sterilized, and are isotonic with respect to blood. In making the pharmaceutical composition into a solution or suspension, all diluents customarily used in the art can be employed. Examples of suitable diluents are water, ethyl alcohol, propylene glycol, ethoxylated isostearyl alcohol, polyoxyethylene sorbitol, and sorbitan esters. Sodium chloride, glucose or glycerol can be incorporated into a therapeutic agent in an amount sufficient to prepare an isotonic solution. The therapeutic agent may further contain ordinary dissolving aids, buffers, pain-alleviating agents, and optionally, coloring agents, fragrances, flavors, sweeteners, and other pharmacologically active agents which are known in the art.

The dosage of the compounds of the present invention can be in the range from about 100 mg to 1,000 mg per adult human by oral administration per day, or from about 1 mg to 100 mg per adult human by parenteral administration per day in multiple doses depending upon the type of diseases, the severity of condition to be treated, and the like.

The present invention is further illustrated in more detail by way of the following Examples. The melting points of the products obtained were uncorrected.

EXAMPLE 1

Methyl 1-amino-4,5-dihydro-5-oxo-4-phenyl-thieno[2,3-c]isoquinoline-2-carboxylate (compound 1)

To a solution of 17.5 g of methyl 2-cyanomethyl benzoate and 16.2 g of phenyl isothiocyanate in 300 ml of tetrahydrofuran was added 4.8 g of a 60% sodium hydride for 20 minutes under an ice-cooling in a stream of nitrogen, and the mixture was stirred for 1 hour at room temperature. To the reaction mixture was added 18.4 g of methyl bromoacetate for 15 minutes, and then the mixture was stirred for 1 hour. To the reaction mixture was added 4.8 g of a 60% sodium hydride, and the mixture was stirred for 14 hours. The reaction mixture was poured into 3 l of water, and the precipitates were collected by a filtration. The precipitates were successively washed with water and acetone, and air-dried, and dried over phosphorus pentaoxide to obtain 25.3 g of the desired product as brown crystals.

Melting point: over 270° C.

IR (KBr) cm$^{-1}$: 3440, 1660, 1615, 1535, 1485, 1425, 1280.

NMR (CDCl$_3$) δppm: 3.79(3H, s), 6.14(2H, brs), 7.3–7.7(6H, m), 7.82(1H, t, J=8.0 Hz), 8.12(1H, d, J=8.0 Hz), 8.56(1H, d, J=8.0 Hz).

EXAMPLE 2

Methyl 1-amino-4,5-dihydro-4-(2-methylphenyl)-5-oxo-thieno[2,3-c]isoquinoline-2-carboxylate (compound 2)

The desired compound was prepared by a similar manner to that described in Example 1 except that 2-methylphenyl isothiocyanate was used in place of phenyl isothiocyanate used in Example 1.

Melting point: 236°–237° C.

IR (KBr) cm$^{-1}$: 3410, 1660, 1645, 1640, 1625, 1620, 1290, 1285.

NMR (CDCl$_3$) δ ppm: 2.13(3H, s), 3.78(3H, s), 6.16(2H, brs), 7.25–7.50(4H, m), 7.57(1H, ddd, J=8.1, 7.1, 1.0 Hz), 7.83(1H, ddd, J=8.1, 7.1, 1.5 Hz), 8.14(1H, d, J=8.1 Hz), 8.58(1H, dd, J=8.1, 1.5 Hz).

Mass (EI): 364(M+).

EXAMPLE 3

Methyl 1-amino-4,5-dihydro-5-oxo-4-phenyl-dithieno[2,3-b:3',2'-d]pyridine-2-carboxylate (compound 3)

Methyl 3-cyanomethylthiophene-2-carboxylate

To a solution of 14.2 g of 2-methylthiophene carboxylic acid in 100 ml of a dry dimethylformamide was added 4.8 g of a 60% sodium hydride for 5 minutes under an ice-cooling, and then to the mixture was 8.72 ml of methyl iodide for 5 minutes. The mixture was stirred for 3 hours at room temperature. The reaction mixture was cooled under an ice-water, and to the cold reaction mixture was added 100 ml of a saturated sodium chloride aqueous solution. The mixture was extracted with 100 ml of diethyl ether twice. The extrate was successively washed with water and a saturated sodium chloride aqueous solution, dried over anhydrous magnesium sulfate, and then concentrated under reduced pressure to obtain an oil. The oil substance obtained was dissolved in 100 ml of carbon tetrachloride, and to the solution were added 17.8 g of N-bromosuccinimide and an adequate amount of benzoyl peroxide as a catalyst. The mixture was refluxed for 8 hours, and then cooled, and insoluble materials were filtered off. The filtrate was successively washed with a 10% sodium thiosulfate aqueous solution twice, a 5% sodium bicarbonate aqueous solution and water, dried over anhydrous magnesium sulfate, and evaporated under reduced pressure to obtain 25.4 g of crystalline raw product. A solution of the crystalline raw product in 66 ml of methanol was added to 22 ml of a aqueous solution containing 4.8 g of potassium cyanide with stirring at room temperature for 5 minutes. The mixture was stirred for 30 minutes, and then heated at 50° C. for 45 minutes with stirring. To the reaction mixture was added 300 ml of ethyl acetate and 150 ml of a 5% sodium bicarbonate aqueous solution, and the mixture was stirred. The organic layer was successively washed with water twice and a saturated sodium chloride aqueous solution, dried over anhydrous magnesium sulfate, and evaporated under reduced pressure to obtain 20.2 g of crystalline raw product. The crystalline raw product was purified by silica gel column chromatography (eluent: hexane/ethyl acetate=10/1) to obtain 9.50 g of the desired product as white crystals.

NMR (CDCl$_3$) δ ppm: 3.90(3H, s), 4.18(2H, s), 7.23(1H, d, J=5.4 Hz), 7.95(1H, d, J=5.4 Hz).

Methyl 1-amino-4,5-dihydro-5-oxo-4-phenyl-dithieno[2,3-b:3',2'-d]pyridine-2-carboxylate (compound 3)

To a solution of 1.81 g of methyl 3-cyanomethylthiophene-2-carboxylate and 1.62 g of phenyl isothiocyanate in 30 ml of tetrahydrofuran was added 480 mg of a 60% sodium hydride with stirring at 0° C. in a stream of nitrogen, and the mixture was stirred for 1 hour at room temperature. To the reaction mixture was added 1.14 ml of methyl bromoacetate at room temperature, and the mixture was stirred for 3 hours. To the reaction mixture was added 480 mg of a 60% sodium hydride, and the mixture was stirred overnight at room temperature. To the reaction mixture was added 100 ml of water, and precipitates were collected by a filtration. The precipitates were successively washed with water, benzene and n-hexane, and dried over to obtain 3.06 g of the desired product as white crystals.

Meting point: 265° C.

IR (KBr) cm$^{-1}$: 1660, 1610, 1540, 1280.

NMR (CDCl$_3$) δ ppm: 3.78(3H, s), 5.98(2H, brs), 7.35-7.45(2H, m), 7.55-7.65(3H, m), 7.63(1H, d, J=5.4 Hz), 7.95(1H, d, J=5.4 Hz).

EXAMPLE 4

Methyl 1-amino-4-(2-chlorophenyl)-4,5-dihydro-5-oxo-thieno[2,3-c]isoquinoline-2-carboxylate (compound 4)

To a solution of 1.85 g of potassium t-butoxide in 32.3 ml of a dry tetrahydrofuran was added 2.83 g of methyl 2-cyanomethylbenzoate with stirring under an ice-cooling in a stream of nitrogen, and then to the mixture was added 3.02 g of 2-chlorophenyl isothiocyanate for 10 minutes. The mixture was stirred under an ice-cooling for 10 minutes. To the reaction mixture was added 2.72 g of methyl bromoacetate for 10 minutes, and the mixture was stirred for 80 minutes at room temperature. The reaction mixture was cooled under an ice-bath, and 363 mg of potassium t-butoxide was added to the cold mixture. The mixture was stirred for 1 hour under an ice-cooling. To the reaction mixture was added 70 ml of water for 2 minutes, and the mixture was stirred for 15 minutes. Precipitates were collected by a filtration, and successively washed with water, methanol and hexane, and dried under reduced pressure to obtain 4.87 g of the desired product as white colorless crystals.

Melting point: 244°-246° C.

IR (KBr) cm$^{-1}$: 3440, 1660, 1615, 1535, 1480, 1280.

NMR (CDCl$_3$) δ ppm: 3.79(3H, s), 6.16(2H, brs), 7.4-7.7(5H, m), 7.83(1H, t, J=8.0 Hz), 8.14(1H, d, J=8.0 Hz), 8.58(1H, d, J=8.0 Hz).

Mass (EI) m/z: 384 (M+).

EXAMPLE 5

Methyl 1-amino-4-(2-bromophenyl)-4,5-dihydro-5-oxo-thieno[2,3-c]isoquinoline-2-carboxylate (compound 5)

The desired compound was prepared by similar manners to those described in Example 1 and Example 4 except that 2-bromophenyl isothiocyanate was used in place of phenyl isothiocyanate used in Example 1 and 2-chlorophenyl isothiocyanate used in Example 4.

Melting point: 214°-216° C.

IR (KBr) cm$^{-1}$: 3420, 3320, 2960, 1650, 1610, 1480, 1270.

NMR (CDCl$_3$) δ ppm: 3.78(3H, s), 6.17(2H, brs), 7.4-7.6(4H, m), 7.7-7.9(2H, m), 8.13(1H, d, J=8.2 Hz), 8.57(1H, d, J=8.2 Hz).

EXAMPLE 6

Methyl 1-amino-4-(2-ethylphenyl)-4,5-dihydro-5-oxo-thieno[2,3-c]isoquinoline-2-carboxylate (compound 6)

The desired compound was prepared by a similar manner to that described in Example 1 except that 2-ethylphenyl isothiocyanate was used in place of phenyl isothiocyanate used in Example 1.

Melting point: 174°-176° C.

IR (KBr) cm$^{-1}$: 3480, 3340, 2960, 1650, 1600, 1475, 1260.

NMR (CDCl$_3$) δ ppm: 1.14(3H, t, J=7.6 Hz), 2.42(2H, q, J=7.6 Hz), 3.77(3H, s), 6.16(2H, brs), 7.26(1H, d, J=7.3 Hz), 7.3-7.6(4H, m), 7.82(1H, t, J=7.3 Hz), 8.14(1H, d, J=8.0 Hz), 8.58(1H, d, J=8.0 Hz).

EXAMPLE 7

Methyl 1-dimethylaminomethyleneamino-4,5-dihydro-5-oxo-4-phenyl-thieno[2,3-c]isoquinoline-2-carboxylate (compound 7)

To a solution o 1.05 g of methyl 1-amino-4,5-dihydro-5-oxo-4-phenyl-thieno[2,3-c]isoquinoline-2-carboxylate in 20 ml of dimethylformamide was added 0.55 g of phosphorus oxychloride at room temperature, and the mixture was stirred for 30 minutes. The reaction mixture was poured into water, and neutralized with a saturated sodium bicarbonate aqueous solution, and precipitates were collected by a filtration. The precipitates were washed with water, and dried under reduced pressure. The residue was purified by silica gel column chromatography to obtain 1.09 g of the desired product as pale yellow crystals (eluent: n-hexane/chloroform=1/1).

Melting point: 225°-227° C.

NMR (CDCl$_3$) δ ppm: 3.14(3H, brs), 3.28(3H, brs), 3.71(3H, s), 7.4-7.8(8H, m), 8.48(1H, d, J=8.1 Hz), 9.17(1H, d, J=8.1 Hz).

EXAMPLE 8

Methyl 1-dimethylaminomethyleneamino-4,5-dihydro-4-(2-methylphenyl)-5-oxo-thieno[2,3-c]isoquinoline-2-carboxylate (compound 8)

Methyl 1-amino-4,5-dihydro-4-(2-methylphenyl)-5-oxo-thieno[2,3-c]isoquinoline-2-carboxylate (1.09 g) which was prepared by a similar manner to that described in Example 2 was treated by a similar manner to that described in example 7 to obtain 1.25 g of the desired product as white colorless crystals.

IR (KBr) cm$^{-1}$: 1690, 1655, 1625, 1625, 1380, 1195.

NMR (CDCl$_3$) δ ppm: 2.13(3H, s), 3.15(3H, brs), 3.28(3H, brs), 3.71(3H, s), 7.25-7.55(5H, m), 7.70(1H, s), 7.73(1H, brt), 8.49(1H, dd, J=8.1, 1.5 Hz), 9.18(1H, d, J=7.6 Hz).

EXAMPLE 9

Methyl 4,5-dihydro-4-(2-methylphenyl)-1-(1-methyl-2-pyrrolidinylideneamino)-5-oxo-thieno[2,3-c]isoquinoline-2-carboxylate (compound 9)

To a solution of methyl 1-amino-4,5-dihydro-4-(2-methylphenyl)-5-oxo-thieno[2,3-c]isoquinoline-2-carboxylate [M.P. 236°–237° C.), 510 mg] in 5 ml of N-methyl-2-pyrrolidone, which was prepared by a similar manner to that described in Example 2, was added 1.57 ml of phosphorus oxychloride at room temperature, and the mixture was stirred for 1 hour. The reaction mixture was poured into 50 ml of water, and neutralized with a saturated sodium bicarbonate aqueous solution. Precipitates were collected by a filtration, washed with water, extracted with chloroform, and dried over anhydrous magnesium sulfate. The solution was evaporated under reduced pressure, and the residue was dried under reduced pressure to obtain 583 mg of the desired product as yellow crystals.

Melting point: 209°–211° C.

IR (KBr) cm$^{-1}$: 3480, 2960, 1700, 1660, 1625, 1525, 1385.

NMR (CDCl$_3$) δ ppm: 1.8–2.3(6H, m), 2.6–2.9(1H, m), 3.22(3H, s), 3.4–3.6(2H, m), 3.71(3H, s), 7.2–7.6(5H, m), 7.72(1H, t, J=8.3 Hz), 8.50(1H, d, J=8.3 Hz), 8.88(1H, d, J=8.3 Hz).

EXAMPLE 10

Methyl 1-amino-4,5-dihydro-4-phenyl-thieno[2,3-c]isoquinoline-2-carboxylate (compound 10)

To a suspension of 0.34 g of lithium aluminum hydride in 30 ml of tetrahydrofuran was added a solution of 1.20 g aluminium chloride in 60 ml of ether for 10 minutes. To the mixture was added a solution of 1.05 g of methyl 1-amino-4,5-dihydro-5-oxo-4-phenyl-thieno[2,3-c]isoquinoline-2-carboxylate in 60 ml of tetrahydrofuran for 50 minutes, which was prepared by Example 1, and the mixture was stirred for 40 minutes. To the reaction mixture was added 30 ml of a 5% sodium hydroxide aqueous solution, and the mixture was stirred. The aqueous layer was extracted with 30 ml of tetrahydrofuran twice. The organic layers were combined together, and dried over anhydrous magnesium sulfate. The dried solution was evaporated under reduced pressure, and the residue was purified by silica gel column chromatography (eluent: n-hexane/chloroform=1/1) to obtain amorphous product in orange-yellow. The amorphous product obtained was triturated with n-hexane to obtain 180 mg of the desired product.

Melting point: 136°–142° C.

IR (KBr) cm$^{-1}$: 3480, 1725, 1660, 1620, 1530, 1380, 1275.

NMR (CDCl$_3$) δ ppm: 3.75(3H, s), 4.75(2H, s), 5.96(2H, brs), 7.1–7.5(8H, m), 7.70(1H, d, J=7.8 Hz).

EXAMPLE 11

Pharmacological Effects

Vasorelaxant Effect (V.R., ED$_{50}$)

Male albino rabbits were killed by exanguination. The superior mesenteric artery was removed immediately and cut into helical strips.

The vascular strips were vertically suspended in an organ bath filled with a Krebs-Henseleit solution the temperature of which was maintained at 37°±0.5° C. A mixture of 95% O$_2$-5% CO$_2$ was constantly bubbled through the bicarbonate-based solution in the organ bath. Mechanical responses of the rabbit mesenteric artery evoked by a high concentration of KCl were measured isometrically using the force-displacement transducer.

After obtaining a reproducible response to KCl, the preparations were precontracted with 20 mM KCl and then relaxed by the cumulative addition of the compounds. The ED$_{50}$ value was read from a plot of the percentage of the relaxing response (maximum contractile response to KCl was taken as 100%) vs. the log concentration of the compounds.

Inhibition of Platelets Aggregation (P.A.IC$_{50}$)

Preparation of washed platelets (centrifugation method) Blood drawn from healthy human volunteers was anticoagulated with 1/10 volume of 0.38% sodium citrate. Platelets-rich plasma (PRP) was obtained by centrifugation of whole blood at 700× G for 10 minutes. The resulting PRP was then centrifuged at 1500× G for 10 minutes in the presence of 1/6 volume of ACD solution (2.2% of sodium citrate, 0.8% of citric acid and 2.2% of glucose), and the pellet was suspended with the modified HEPES-Tyrode solution (135 mM NaCl, 2.7 mM KCl, 1 mM MgCl$_2$, 0.1% glucose, and 20 mM HEPES; pH 7.4).

After the platelet suspension was centrifuged again at 1500× G for 5 minutes with 1/6 volume of the ACD solution, the pellet was resuspended with the modified HEPES-Tyrode solution. Then the washed platelet suspension (=300,000 platelets/μl) was obtained.

Measurement of Platelet Aggregation (Turbidmetric Method)

Platelet aggregation was studied by the turbidmetric method with an 4 ch. aggregometer (HEMA tracer 601; Nikoh Bioscience Co., Japan). Test sample (3 μl, appropriate concentration) or vehicle (3 μl) was added to 270 μl of the platelet suspension and incubated at 37° C. with stirring for 2 minutes before the addition of 30 μl collagen (20 μl/ml).

Estimation of Inhibitory Action

The extent of aggregation was expressed by the maximum change of light transmission expressed as a percentage, taking the difference between light transmission for the platelet suspension and platelet-poor-plasma as a value of 100%. Percent inhibition of aggregation by a test compound was calculated by dividing the percent aggregation by that observed in the control run, then multiplying by 100. IC$_{50}$ values were expressed as the concentrations of test compounds which produced 50% inhibition of the platelet aggregation.

Results obtained were as follows:

| Test Compound | P.A.IC$_{50}$ (μM) | V.R.ED$_{50}$ (μM) |
| --- | --- | --- |
| compound 1 | 0.023 | 20 |
| compound 2 | 0.56 | 4.6 |
| compound 3 | 0.26 | — |
| compound 4 | 0.1 | 5.7 |
| compound 7 | 100 | 74 |
| compound 8 | — | 1.6 |
| compound 9 | 100 | 1.1 |
| compound 10 | 0.31 | 8.0 |

The compounds of the present invention have also inhibitory effects on the various enzymes such as cAMP-dependent protein kinase, myosin light chain kinase, protein kinase C, calmodulin-dependent protein

What is claimed is:

1. A compound represented by the formula:

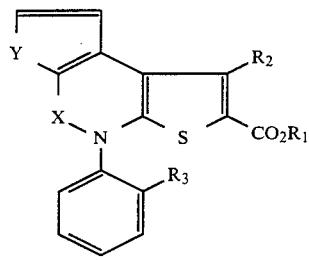

wherein $R_1$ represents an alkyl group having 1 to 3 carbon atoms, $R_2$ represents an amino group or a group of formula

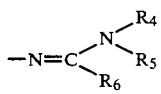

in which $R_4$ represents an alkyl group having 1 to 3 carbon atoms, $R_5$ represents an alkyl group having 1 to 3 carbon atoms or may combine with $R_6$ to form a five or six membered ring containing 4 to 5 carbon atoms, $R_6$ represents a hydrogen atom or may combine with $R_5$ to form a five or six membered ring containing 4 to 5 carbon atoms, $R_3$ represents a hydrogen atom, an alkyl group having 1 to 3 carbon atoms or a halogen atom, X represents a carbonyl group or a methylene group, Y represents a sulfur atom or a vinylene group and pharmaceutically acceptable salts thereof.

2. The compound as claimed in claim 1, represented by the formula:

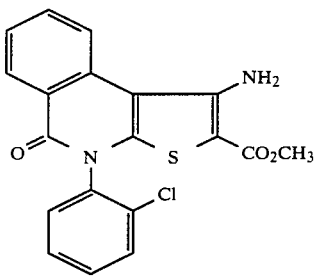

and a pharmaceutically acceptable salt thereof.

3. The compound as claimed in claim 1, represented by the formula:

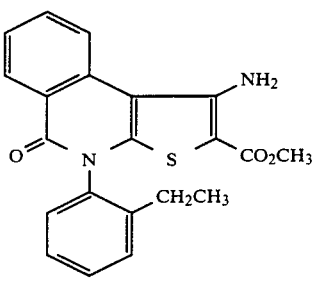

and a pharmaceutically acceptable salt thereof.

4. The compound as claimed in claim 1, represented by the formula:

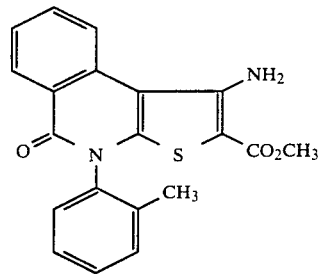

and a pharmaceutically acceptable salt thereof.

5. The compound as claimed in claim 1, represented by the formula:

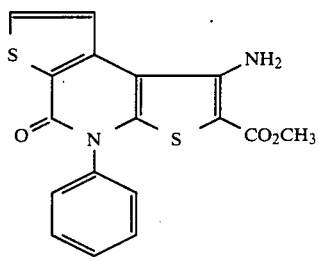

and a pharmaceutically acceptable salt thereof.

6. The compound as claimed in claim 1, represented by the formula:

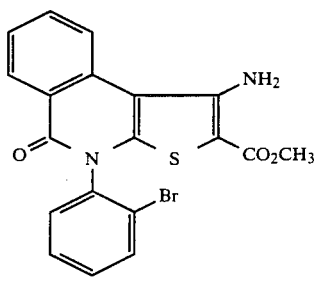

and a pharmaceutically acceptable salt thereof.

7. The compound as claimed in claim 1, represented by the formula:

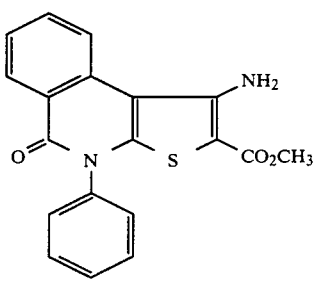

and a pharmaceutically acceptable salt thereof.

8. The compound as claimed in claim 1, represented by the formula:

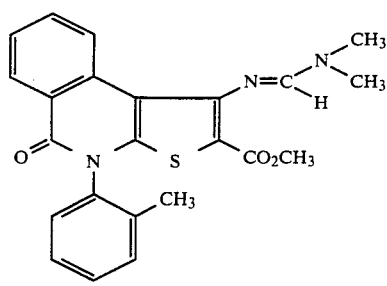

and a pharmaceutically acceptable salt thereof.

9. The compound as claimed in claim 1, represented by the formula:

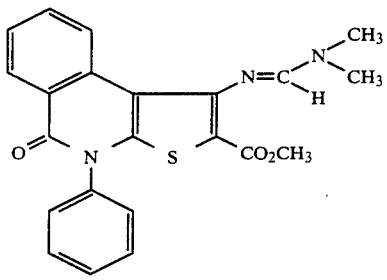

and a pharmaceutically acceptable salt thereof.

10. The compound as claimed in claim 1, represented by the formula:

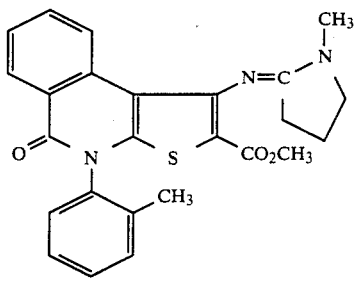

and a pharmaceutically acceptable salt thereof.

11. The compound as claimed in claim 1, represented by the formula:

and a pharmaceutically acceptable salt thereof.

* * * * *